United States Patent [19]

Campbell et al.

[11] Patent Number: 4,744,954
[45] Date of Patent: May 17, 1988

[54] AMPEROMETRIC GAS SENSOR CONTAINING A SOLID ELECTROLYTE

[75] Inventors: Donald N. Campbell, Timonium; Robert C. Davis, Jr., Westminster; John C. Schmidt, Baltimore, all of Md.

[73] Assignee: Allied-Signal Inc., Morristown, N.J.

[21] Appl. No.: 884,582

[22] Filed: Jul. 11, 1986

[51] Int. Cl.$^4$ ............................................. G01N 27/12
[52] U.S. Cl. ..................................... 422/98; 204/421; 204/431; 422/90; 436/151
[58] Field of Search .......................... 422/90, 98, 54; 436/151; 204/412, 421, 431

[56] References Cited

U.S. PATENT DOCUMENTS

| | | |
|---|---|---|
| 2,795,716 | 6/1957 | Roberts . |
| 3,372,994 | 3/1968 | Giuffrida . |
| 3,423,181 | 1/1969 | Dimick et al. . |
| 3,535,088 | 10/1970 | Zimmerman . |
| 3,589,869 | 6/1971 | Scolnick . |
| 3,607,096 | 9/1971 | Hartman . |
| 3,615,237 | 10/1971 | Speakman . |
| 3,677,709 | 7/1972 | Riedman et al. . |
| 3,751,968 | 8/1973 | Loh et al. ........................... 422/90 |
| 3,776,832 | 12/1973 | Oswin et al. . |
| 3,852,037 | 12/1974 | Kolb et al. . |
| 3,925,183 | 12/1975 | Oswin ............................ 204/195 R |
| 4,129,418 | 12/1978 | Davis ................................... 422/98 |
| 4,130,797 | 12/1978 | Hattori et al. ....................... 422/98 |
| 4,184,937 | 1/1980 | Tataria ........................... 204/195 R |
| 4,202,666 | 5/1980 | Hall et al. ............................ 422/98 |
| 4,203,726 | 5/1980 | Patterson ............................. 422/98 |
| 4,521,287 | 6/1985 | Kisner ........................... 204/192.25 |
| 4,522,690 | 6/1985 | Venkatasetty ................... 204/412 |
| 4,524,047 | 6/1985 | Patterson ............................. 422/98 |
| 4,650,560 | 3/1987 | Ueno ................................. 204/412 |

OTHER PUBLICATIONS

M. Lederer, "Chromatographic Reviews", vol. 12, (1970), pp. 6-39.
S. Davidson, "Progress in Surface Science", vol. 1, Pergamon Press, N.Y., '72.
R. C. Hall, "CRC Critical Reviews in Analytical Chemistry", (12/78), pp. 323-380.
M. E. Scolnick, "The Chemi-Ionization Detector: A Flameless Ionization Detector", Jrnl. of Chromatographic Sci., vol. 8, (8/70), pp. 462-466.
B. Kolb, "Reaction Mechanism in an Ionization Detector, etc.", Jrnl. of Chromatographic Sci., vol. 15, (2/77), pp. 53-63.
Kolb and Bischoff, Jrnl. Chromatographic Sci., 12:625, (1974).
E. Zandberg, "Surface Ionization", (3 and 4 '59), Soviet Physics Uspehki, vol. 67(2), #2, pp. 255-281.
N. Ionov, "Surface Ionization and its Applications", Prog. in Surface Science, vol. 1, Pergamon Press, NY (1972).
M. Kaminsky, "Atomic & Ionic Impact Phenomena on Metal Surfaces", Academic Press, N.Y., (965), pp. 99-378.
E. Zandberg, "Surface Ionization of Organic Compounds", Russian Chem. Revs., 51(9), (9/82), pp. 819-832.
P. Kebarle, "Higher Order Reactions—Ion Clusters & Ion Solvation", Ion-Molecule Reactions, vol. 1, Ed by J. Franklin, Plenum Press, N.Y., (1972), pp. 315-353.
P. Patterson, "Selective Responses of a Flameless Thermionic Detector", Jrnl. of Chromatog., 167, (1978), pp. 381-397.
R. Weiting, "Reactions of Alkali Ions with Organic Molecules in the Gas Chamber", Jrnl. Amer. Chem. Soc., 97:4, (2/75), p. 924.
R. Staley, "Intrinsic Acid-Base Prop. of Molecules, etc.", Jrnl. Amer. Chem. Soc., 97:20, (10/75), pp. 5920-5921.
J. Plambeck, Electroanalytical Chemistry, Wiley-Interscience, New York, NY, (1982), pp. 50-51.

*Primary Examiner*—Michael S. Marcus
*Attorney, Agent, or Firm*—Robert M. Trepp; Bruce L. Lamb

[57] ABSTRACT

An electrochemical gas sensor is described incorporating a sensing electrode, a reference electrode, a solid matrix containing an alkali salt, a potentiostat and a heater. The invention overcomes the problem of a liquid electrolyte which may operate over limited environmental conditions.

8 Claims, 2 Drawing Sheets

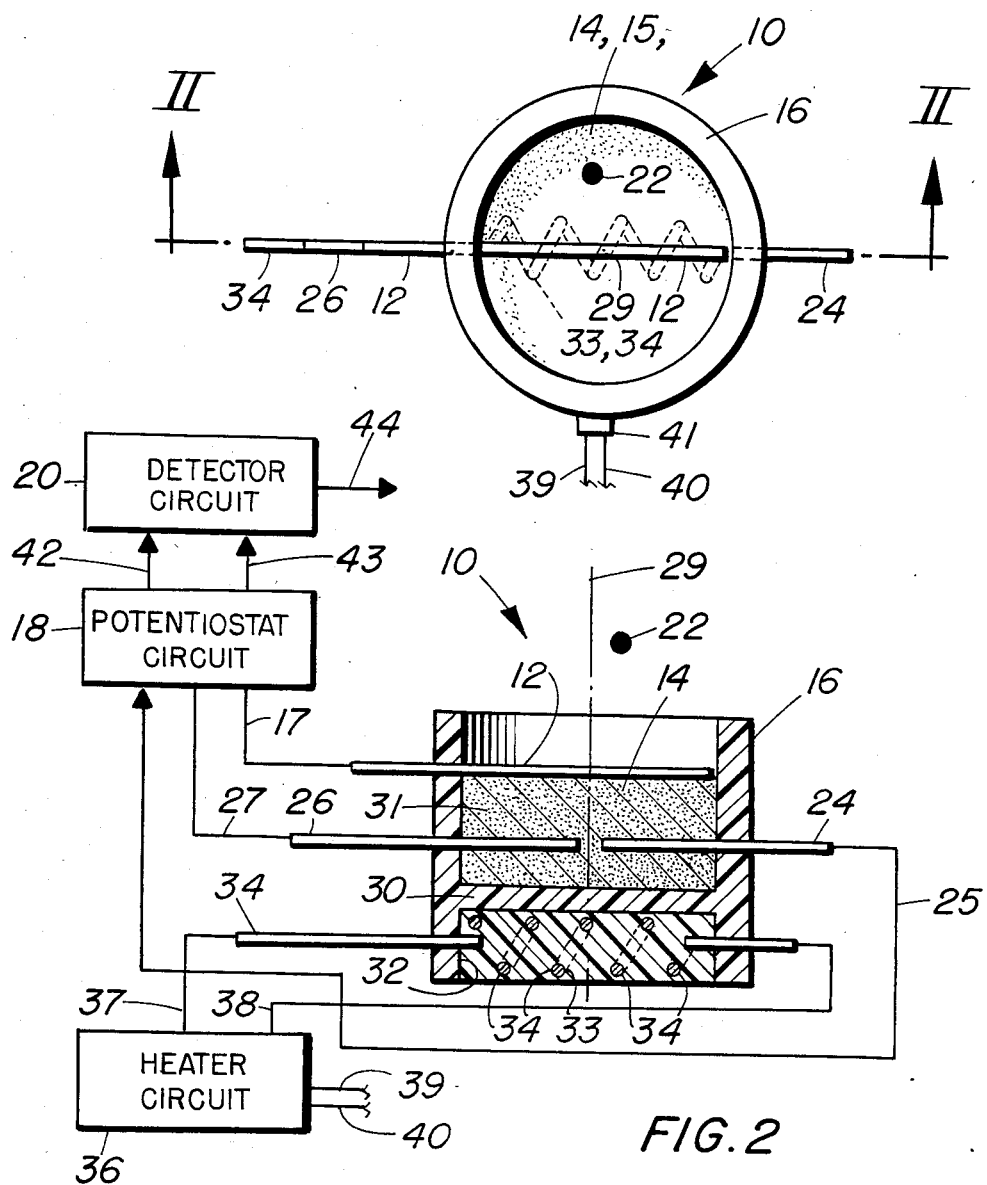

AMPEROMETRIC GAS SENSOR CONTAINING A SOLID ELECTROLYTE

CROSS REFERENCE TO A RELATED APPLICATION

Cross reference is made to U.S. application Ser. No. 701,898, filed on Feb. 15, 1985, entitled "Selective Ionization of Gas Constituents Using Electrolytic Reactions" by K. N. Vora et al. and assigned to the assignee herein and directed to an electrolytic ionization source using inorganic/organic salts which react with sample molecules to form product ions. The electrolytic ionization source is selective and may be used for example in an ion mobility spectrometer, an ionization detector and a mass spectrometer.

BACKGROUND OF THE INVENTION

1. Field of the Invention:

This invention relates to gas sensors and more particularly to an amperometric gas sensor for detecting vapors of organophosphorous compounds in air.

2. Description of the Prior Art:

U.S. Pat. No. 4,203,726, which issued on May 20, 1980 to P. L. Patterson, describes a thermionic detector having a hardened ceramic cement bead impregnated with an alkali metal which is heated in a gaseous environment in the range of 400° C. to 1000° C., whereby a sample interacts with the bead to form negative ions or positive ions. The bead may contain: $Na_2SO_4$, $K_2SO_4$, $Rb_2SO_4$, $Cs_2SO_4$.

U.S. Pat. No. 4,202,666, which issued on May 13, 1980 to R. C. Hall et al., describes an alkali source 10, which is preferably a mixture of alkali salts in a silica gel matrix fused to an electrical resistance heater element.

U.S. Pat. No. 4,129,418, which issued on Dec. 12, 1978 to W. D. Davis, describes an halogen detector in which the active alkali metal compound is independently heated. Typical alkali metal compounds include alkali metal aluminate, carbonate and silicate and, in particular, sodium carbonate and rubidium carbonate.

U.S. Pat. No. 3,925,183, which issued on Dec. 9, 1975 to H. G. Oswin, describes an electrochemical cell for detecting gas which includes a heat reservoir for maintaining the electrochemical cell at substantially constant temperature.

U.S. Pat. No. 3,852,037, which issued on Dec. 3, 1974 to B. Kolb et al., describes an ionization detector including an alkali source in the form of a heated alkali-containing glass which is maintained in a heated softened state during operation of the detector.

U.S. Pat. No. 3,776,832, which issued on Dec. 4, 1973 to H. G. Oswin et al., which reissued as U.S. Pat. No. Re. 31,916 on June 18, 1985, describes a three electrode electrochemical gas sensor which can be adapted to measure oxidizable or reducible gases, such as chlorine, CO, $Cl_2$ and hydrazine, as well as other gases. This particularly known cell has two shortcomings. First, it requires an aqueous electrolyte which has a limited service life due to evaporation of the electrolyte. Secondly, the temperature range within which the cell can operate is limited due to the possibility of freezing the electrolyte. Thirdly, a complicated structure is required to retain the liquid electrolyte in the sensor.

U.S. Pat. No. 3,677,709, which issued on July 18, 1972 to M. Riedmann et al., describes a flame ionization detector including a piece of salt supported in a collector ring. The salt may be rubidium sulfate or rubidium bromide for detecting nitrogen and phosphorous. The salt may be cesium sulfate or cesium iodine for detecting substances containing chromium chlorine, bromide and iodine.

U.S. Pat. No. 3,615,237, which issued on Oct. 26, 1971 to F. P. Speakman, describes a thermionic flame ionization detector including a flame seeding material such as of the alkali halides, for example, bromine and sulfate salts of sodium, cesium, potassium and rubidium.

U.S. Pat. No. 3,607,096, which issued on Sept. 21, 1971 C. H. Hartman, describes an alkali flame ionization detector which uses an alkali salt such as rubidium sulfate, potassium bromide, rubidium bromide, cesium bromide and potassium sulfate.

U.S. Pat. No. 3,589,869, which issued on June 29, 1971 to M. E. Scolick, describes a chemical ionization detector wherein a non-hydrocarbon constituent of the sample to be detected is reacted with an alkali metal vapor in a reaction zone by the application of heat supplied by a heater. At column 3, starting at line 56, the alkali reactive material may be one of the following alkali salts: cesium bromide, nitrate or chloride, potassium bromide or chloride, rubidium bromide, fluoride, or sulfate, or sodium bromide or chloride.

U.S. Pat. No. 3,535,088, which issued on Oct. 20, 1970 to H. Zimmermann, describes a flame ionization detector including a hollow body for holding an alkali compound such as $K_2Cr_2O_4$ or $KMnO_4$.

U.S. Pat. No. 3,423,181, which issued on Jan. 21, 1969 to K. P. Dimick et al., describes a flame ionization detector using a salt of an alkali or alkaline earth metal as an ion source such as cesium bromide.

U.S. Pat. No. 3,372,994, which issued on Mar. 12, 1968 to L. E. Giuffrida, describes a hydrogen flame ionization detector using a heated electrode coated with a fused alkali metal salt.

U.S. Pat. No. 2,795,716, which issued on June 11, 1957 to J. A. Roberts, describes a vapor detector embodying a positive ion source. A coating 15 of positive ion emitting material is provided on a ceramic core 12 and heated by heater coil 13. Coating 15 may be an alkali metal glass, such as alumino-silicates of the alkali metals (Li, Na, K, Rb, Cs), which provide positive ions as described in column 3 at lines 24–40.

In the publication by M. Lederer, "Chromatographic Reviews", Vol. 12 (1970), pgs. 6–39, thermionic detectors are discussed. On pages 13–16 the relationship between the sensitivity of the thermionic detector and the alkali salt used is discussed, See for example Table II on page 14.

In the publication by R. C. Hall, "CRC Critical Revs. in Analytical Chemmistry" (12/78), pgs. 323–380, an alkali flame detector is shown in FIG. 8 and discussed on pages 325-30. A flameless alkali sensitized detector is shown in FIGS. 10–11 and discussed on pages 330–344. Electrochemical detectors are discussed on pages 344–366 with a block diagram of an electrolytic conductivity detector shown in FIG. 33.

In the publication to M. E. Scolnick, "The Chemi-Ionization Detector: A Flameless Ionization Detector''—Journal of Chromatographic Sci., Vol. 8 (8/70), pgs. 462–466, FIG. 1 shows a chemi-ionization detector (CID) using cesium bromide and glass beads to provide cesium bromide vapor in the reaction zone which may be heated in the range from 800° C. to 850° C.

In the publication by B. Kolb, M. Auer and P. Pospisil, "Reaction Mechanism in an Ionization Detector, etc."—Journal of Chromatographic Sci., Vol. 15, (2/77) pgs. 53-63, FIG. 1 shows an alkali flame detector wherein the alkali source is a small glass bead which contains rubidium silicate.

In a publication by Kolb and Bischoff, J. Chromatog. Sci 12:625-29 (1974), a nitrogen-phosphorous detector (NPD) was briefly described.

In the publication by E. Y. Zandberg and N. I. Ionov, "Surface Ionization" (Mar.-Apr. '59), Soviet Physics Uspehki, Vol. 67(2), #2, pgs. 255-281, positive surface ionization without alkali metal atoms and alkali halide molecules on the surface of tungsten and platinum is discussed starting at pages 263-270. Positive surface ionization in electric fields is discussed on pages 270-272. Negative surface ionization is discussed on pages 274-279.

In a publication by E. Y. Zandberg, surface ionization of molecules is discussed on pages 1135 and 1136. Surface ionization in strong electric fields is discussed on pages 1136 and 1137. Surface ionization of organic compounds in weak electric fields is discussed on pages 1137-1140.

In a publication N. I. Ionov, "Surface Ionization and Its Applications," in: Progress in Surface Science, Vol. 1, Pergamon Press, New York (1972), the surface ionization of molecules is discussed on pages 301-311.

In a publication by M. Kaminsky, "Atomic & Ionic Impact Phenomena on Metal Surfaces", Academic Press, N.Y. (1965), pgs. 99-378, positive surface ionization of alkali metal atoms in weak electric fields is discussed on pages 117-124. Positive surface ionization of some alkali-salt molecules on metal surfaces in weak external fields is discussed on pages 124-127. Positive surface ionization of alkaline earth elements and compounds in weak external fields is discussed on pages 127-130.

In a publication by E. Y Zandberg and U. K. Rasulev, "Surface Ionization of Organic Compounds", Russian Chemical Revs. 51 (9), Sept. 1982, pgs. 819-832, the characteristics of surface ionization of organic compounds is discussed on pages 820-822.

In a publication by P. Kebarle, "Higher-Order Reactions—Ion Clusters & Ion Solvation", Ion-Molecule Reactions, Vol. 1, Ed. by J. L. Franklin, Plenum Press, N.Y. (1972), pgs. 315-353, gas-phase hydration of alkali and halide ions are discussed on pages 341-345.

In the publication by P. L. Patterson, "Selective Responses of a Flameless Thermionic Detector," Journal of Chromatography, 167 (1978) pgs. 381-397, a schematic diagram of a thermionic detector having a hot bead is shown in FIG. 1. The hot bead which may be an alkali metal-ceramic bead is discussed on pages 382 and 383.

In a publication by R. D. Wieting et al., "Reactions of Alkali Ions With Organic Molecules in the Gas Phase", Journal Amer. Chem. Society, 97:4, (2/19/75), pg. 924, reactions of alkali ions with organic molecules in a gas phase are discussed.

In a publication by R. H. Staley and J. L. Beauchamp, "Intrinsic Acid-Base Properties of Molecules etc.", Journal Amer. Chem. Society, 97:20, (10/1/75), pgs. 5920-5921, intrinsic acid-base properties of molecules is discussed. The binding energies of lithium ions to certain molecules is shown in FIG. 1.

U.S. Pat. No. 4,184,937, which issued on Jan. 22, 1980, to H. Tataria et al. entitled "Electrochemical Cell for the Detection of Chlorine", describes a three electrode electrochemical cell with a non-aqueous electrolyte consisting preferably of lithium perchlorate dissolved in an organic solvent selected from the group consisting of gamma-butyrolactone and propylene carbonate. The non-aqueous electrolyte has a considerably lower freezing point and vapor pressure than an aqueous electrolyte. The electrodes for use in the two or three electrode electrochemical cells are comprised of either gold or platinum black.

In a publication by J. A. Plambeck, published in *Electroanalytical Chemistry,* Wiley-Interscience, pages 50-51, New York, N.Y. (1982), a potentiostat is described for maintaining a sensing electrode of an electrochemical cell at a fixed potential with respect to its reference electrode.

It is therefore desirable to use an electrolyte in an electrochemical gas sensor which is solid and operable over a wide range of environmental conditions.

It is further desirable to provide a solid electrolyte in an electrochemical gas sensor which is stable, will not decompose, has a high boiling temperature and a low vapor pressure in the liquid and solid state.

It is further desirable to provide an electrolyte in an electrochemical gas sensor which provides structural support to electrodes.

It is further desirable to provide a solid electrolyte in an electrochemical gas sensor which includes an alkali salt embedded in a refractory cement or ceramic matrix to provide a structurally self-supporting structure.

It is further desirable to provide a solid electrolyte including an alkali salt in an electrochemical gas sensor to improve the specificity of the gas sensor.

It is further desirable to reduce the complexity of prior art electro-chemical gas sensors by replacing the liquid electrolyte, and its associated seals and reservoir, with a solid electrolyte.

SUMMARY OF THE INVENTION

An apparatus is described for sensing selected gas constituents of an ambient gas comprising a sensing electrode exposed to the ambient gas, a reference electrode spaced apart from the sensing electrode, in a matrix containing an alkali salt in electrical contact with the sensing electrode and the reference electrode, a potentiostat circuit for maintaining a predetermined voltage on the sensing electrode with respect to the reference electrode, a heater element for heating the alkali salt to at least a predetermined temperature, whereby the alkali salt conducts electricity, and a detector circuit responsive to electric current from the sensing electrode to provide an indication of the concentration of a gas constituent in the ambient gas.

BRIEF DESCRIPTION OF THE DRAWING

FIG. 1 is a plan view of one embodiment of the invention.

FIG. 2 is a cross section view along the lines II—II of FIG. 1.

DESCRIPTION OF THE PREFERRED EMBODIMENT

Figure 3:
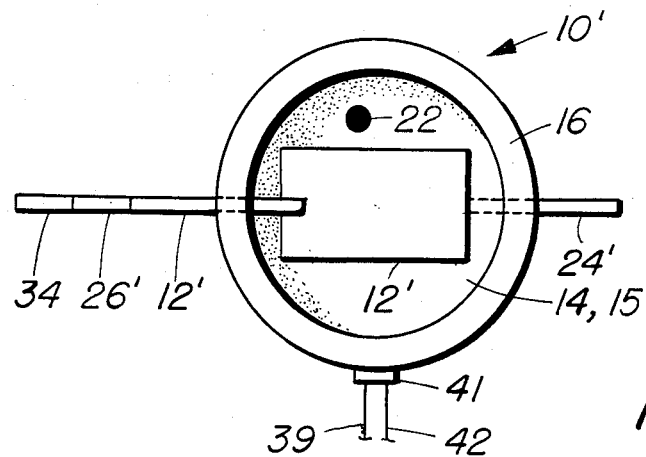
FIG. 3 is a plan view of an alternate embodiment of the invention.

Referring to FIG. 1, an electrochemical gas sensor 10 is shown. FIG. 2 shows a cross sectional view along the lines II-II of FIG. 1. A sensing electrode 12, which may be for example a platinum wire, is shown positioned on and in contact with upper surface 15 of electrolyte 14, which is contained within housing 16. Sensing electrode 12 extends through housing 16 for electrical connection with potentiostat circuit 18 shown in FIG. 2. Sensing electrode 12 and electrolyte 14 are exposed to ambient gas 22 which may be, for example, at atmospheric pressure.

A reference electrode 24 is shown in FIG. 2 spaced apart from sensing electrode 12 and in contact with electrolyte 14. Reference electrode 24 may extend through housing 16 and be coupled over lead 25 to an input of potentiostat circuit 18. Counter electrode 26 is spaced apart from sensing electrode 12 and from reference electrode 24 and is in contact with electrolyte 14. Counter electrode 26 may extend through housing 16 and be coupled over lead 27 to potentiostat circuit 18. Potentiostat circuit 18 functions to maintain a predetermined voltage on sensing electrode 12 with respect to reference electrode 24. Potentiostat circuit 18 provides a current from counter electrode 26 through electrolyte 14 to sensing electrode 12 to maintain the voltage of sensing electrode 12 with respect to reference electrode 24.

Housing 16 may be, for example, a cylinder having open ends with a wall or partition 30 transverse to the longitudinal axis 29 of housing 16 and dividing housing 16 to form cavities 31 and 32. A heating element 33 may be placed in cavity 32 for heating electrolyte 14 to a predetermined temperature, for example to a temperature of 465° C. or above, whereby electrolyte 14 becomes ionically conductive. Heating element 33 may comprise resistance wire 34, which may be, for example, wire including alloys of nickel and chromium. Resistance wire 34 may be coupled to heater circuit 36 via leads 37 and 38. The temperature of electrolyte 14 may be sensed by temperature sensor 41 shown in FIG. 1 which may be positioned on the outside of housing 16. Alternately, temperature sensor 41 may be positioned on the inside of housing 16. Temperature sensor 41 has leads 39 and 40 which are coupled to heater circuit 36. Heater circuit 36 may respond to the signal from temperature sensor 41 to control the current in leads 37 and 38 in wire 34 to maintain electrolyte 14 at a constant predetermined temperature.

Figure 4:
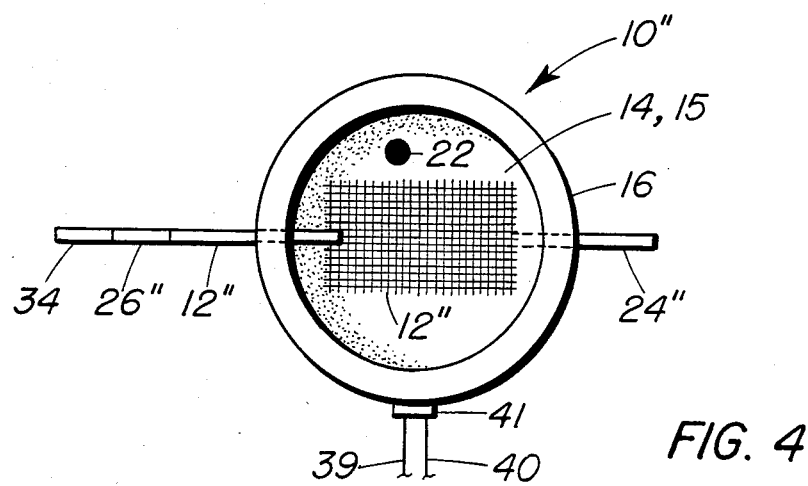
FIG. 4 is a plan view of an alternate embodiment of the invention.

As shown in FIG. 2, detector circuit 20 has an input coupled over leads 42 and 43 from potentiostat circuit 18 and an output on lead 44. Detector circuit 20 functions to provide a signal on lead 44 indicative of the concentration of a gas constituent in the ambient gas 22. The signal may be a function of the electric current passing between sensing electrode 12 and counter electrode 26. One example of a potentiostat circuit 18 and a detector circuit 20 for a three electrode electrochemical cell is shown in FIG. 4 of U.S. Pat. No. 4,525,266, which issued on June 25, 1985, to Schmidt et al. and assigned to the assignee herein, which is incorporated herein by reference.

Electrolyte 14 may be a solid electrolyte including an alkali salt wherein the alkali ion may be selected from the group consisting of lithium, sodium, potassium, rubidium, cesium, francium, calcium and barium. The alkali salt may be mixed with a refractory cement, for example Dylon-C10, available from Dylon Industries, Inc. of Cleveland, Ohio to form a matrix. An alkali salt suitable for mixing with a refractory cement may be for example cesium bromide, rubidium sulfate or rubidium nitrate. Other alkali salts may include: alkali halogen salts, for example, cesium iodide ($C_s$), potassium iodide (KI) etc; alkali acid salts, for example, cesium sulfate ($Cs_2SO_4$), potassium nitrate ($KNO_3$), lithium phosphate ($Li_3PO_4$), etc; and alkaline earth salts, for example, calcium sulfate ($CaSO_4$), barium chloride ($B_aCl_2$), etc. Another refractory cement suitable for mixing with an alkali salt to form a mixture or matrix is Sauereisen 29 cement, available from Sauereisen Co., Pittsburgh, Penna. Electrolyte 14 may be, for example, 10% rubidium sulfate homogeneously dispersed throughout Dylon C-10 refractory cement with three platinum wire electrodes embedded in electrolyte 14 to form electrodes 12, 24 and 26 shown in FIG. 2.

Electrodes 12, 24 and 26 may be other shapes other than wire. For example, FIG. 3 is a plan view of electrochemical gas sensor 10', where electrodes 12', 24' and 26' may be in the form of a metal foil, such as platinum foil, and in various geometric shapes for example a rectangle, square, ellipse or circle. Alternatively, electrodes 12', 24' and 26' may be formed by vacuum sputtering or depositing metal to form thin films of platinum or gold onto surfaces of electrolyte 14 prior to embedding electrodes 26' and 24' with more electrolyte 14 over top.

FIG. 4 is a plan view of electrochemical gas sensor 10". In FIG. 4 electrochemical gas sensor 10' has electrodes 12", 24" and 26" made of wire mesh or screen which may be of various geometric shapes for example a rectangle, square, ellipse, or circle. The mesh or screen may be made out of platinum, gold, or other suitable material or alloy thereof.

In operation of electrochemical gas sensor 10, shown in FIGS. 1 and 2, heater circuit 36 applies power to heater element 33 to raise electrolyte 14 to a predetermined temperature, such as 460° C. or above. Potentiostat circuit 18 maintains the voltage of sensing electrode 12 with respect to reference electrode 24 at a predetermined voltage, for example, in a range from $-1.0$ V to $+1.2$ V. Electrolyte 14 may be composed of 10% rubidium sulfate mixed with a refractory cement, such as Dylon C-10. Ambient gas 22 having selected gas constituents are in the region above electrode 12 and electrolyte 14.

Figure 5:
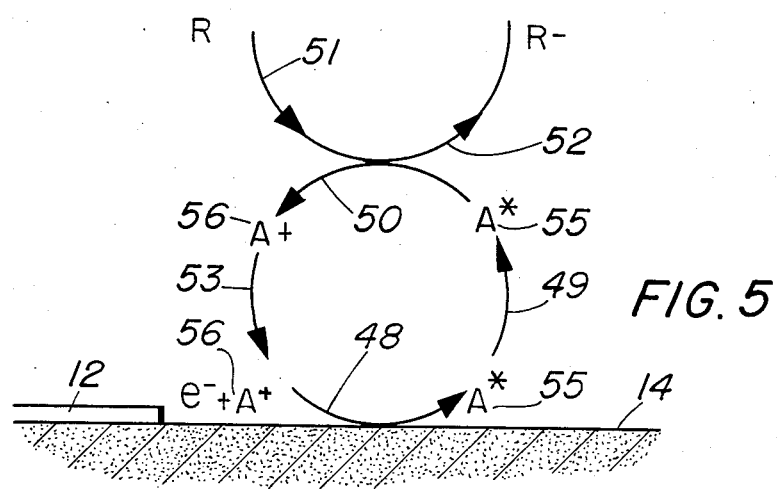
FIG. 5 is a diagram depicting operation of the sensor shown in FIGS. 1, 3 and 4.

The detection mechanism of electrochemical gas sensor 10 may be similar to the well known thermionic detector. Referring to FIG. 5, a diagram is shown depicting operation of electrochemical gas sensor 10. First, an alkali cation 56 is neutralized and evaporates from electrolyte 14 as atom 55, as shown by arrows 48 and 49. Any material more electronegative than the alkali atom 55, such as organophosphorous compounds, for example G or V agents, will reoxidize alkali atom 55 as to alkali cation 56, shown by arrow 50. The gas constituent atom or molecule is indicated in FIG. 5 by R. The gas constituent goes from a neutralized state R, shown by arrow 51, prior to reacting with the alkali atom to an ion $R^-$, shown by arrow 52, after receiving an electron from alkali atom 55, $A^*$, which becomes an alkali cation 56, $A^+$. The alkali cation $A^+$ returns to electrolyte 14 or electrode 12, where the alkali cation 56 is neutralized as shown by arrows 48 and 53. The neutralized alkali atoms 55, previously alkali cation 56, result in a current flow in sensor 12 which is proportional to the concentration of the gas constituents R which are more electronegative than the alkali atom 55.

Data was recorded for typical operation of electrochemical gas sensor 10, shown in FIG. 1, where the ambient gas 22 comprised one of several test gases shown in Table I. The temperature of the electrolyte 14 for each test is shown in Table I. With a zero millivolt voltage applied to electrode 12 by potentiostat circuit 18, the currents from electrode 12 are shown in Table I as measured be detector circuit 20.

TABLE I

| Temperature | Test Gas | Current (uA) |
|---|---|---|
| 463° C. | Acetone | +1 |
| 463° C. | DMMP | 55 |
| 463° C. | Water | 0 |
| 461° C. | Methanol | 0 |
| 461° C. | Malathion | 7 |
| 470° C. | Phosdorin | −17 |

An electrochemical gas sensor has been described for detecting selected compounds in a gaseous environment comprising a sensing electrode exposed to said gaseous environment, a reference electrode spaced apart from said sensing electrode, a matrix containing an alkali salt in electrical contact with the sensing electrode and the reference electrode, a potentiostat for maintaining a predetermined voltage on the sensing electrode with respect to the reference electrode, a heater for heating the alkali salt to at least a predetermined temperature whereby the alkali salt conducts electricity, and means responsive to electric current from the sensing electrode to provide an indication of the concentration of a gas constituent in the gaseous environment.

The invention claimed is:

1. Apparatus for sensing selected gas constituents of an ambient gas comprising:
   a sensing electrode having a surface positioned and arranged to be exposed to said ambient gas,
   a reference electrode spaced apart from said sensing electrode,
   a counter electrode spaced apart from said sensing electrode and said reference electrode,
   an alkali salt in the solid state in physical and electrical contact with said sensing electrode, said reference electrode and said counter electrode,
   circuit means including means for providing a current from said counter electrode through said alkali salt to said sensing electrode to maintain a predetermined voltage on said sensing electrode with respect to said reference electrode.
   means for heating said alkali salt to at least a predetermined temperature at which said alkali salt conducts electricity, and means responsive to electric current from said sensing electrode to provide an indication of the concentration of a gas constituent in said ambient gas.

2. The apparatus of claim 1 wherein said sensing electrode includes a metal wire.

3. The apparatus of claim 1 wherein said sensing electrode includes a metal foil.

4. The apparatus of claim 1 wherein said sensing electrode includes a thin film of metal.

5. The apparatus of claim 1 wherein said sensing electrode includes metal deposited on said alkali salt by vacuum sputtering.

6. The apparatus of claim 1 wherein said sensing electrode includes a wire mesh.

7. The apparatus of claim 1 wherein said counter electrode includes metal deposited on said alkali salt by vacuum sputtering.

8. The apparatus of claim 1 wherein said counter electrode includes a wire mesh.

* * * * *